United States Patent [19]

Gahan

[11] Patent Number: 5,006,284

[45] Date of Patent: Apr. 9, 1991

[54] GRANULES OF ALKYL ESTERS CONTAINING HYDROXYPHENYL GROUPS

[75] Inventor: Michael Gahan, Mobile, Ala.

[73] Assignee: Ciba-Geigy Corporation, Ardsley, N.Y.

[21] Appl. No.: 366,819

[22] Filed: Jun. 14, 1989

[51] Int. Cl.$^5$ .................................... B29B 9/10
[52] U.S. Cl. ............................ 264/9; 264/13; 264/14
[58] Field of Search .......................... 264/9, 13, 14

[56] References Cited

U.S. PATENT DOCUMENTS

| | | | |
|---|---|---|---|
| 2,668,326 | 2/1954 | Schlaudecker | 264/9 |
| 3,037,239 | 6/1962 | Krieger et al. | 264/9 |
| 3,071,815 | 1/1963 | MacKinnon | 264/9 |
| 3,285,855 | 11/1966 | Dexter et al. | 252/57 |
| 3,305,474 | 2/1967 | Knowles et al. | 264/14 |
| 3,308,211 | 3/1967 | Plastridge | 264/9 |

*Primary Examiner*—Mary Lynn Theisen
*Attorney, Agent, or Firm*—Harry Falber

[57] ABSTRACT

A process for the manufacture of granules of low-melting alkyl esters containing hindered hydroxyphenyl groups which comprises introducing a melt of the compound into a cold aqueous solution of an organic water-miscible solvent, thereby obtaining free-flowing and dust-free granules.

13 Claims, No Drawings

GRANULES OF ALKYL ESTERS CONTAINING HYDROXYPHENYL GROUPS

The invention relates to a process for the manufacture of granules of low-melting alkyl esters containing hindered hydroxyphenyl groups, and to the free-flowing, dust-free granules of said compounds.

Alkyl esters containing a hindered hydroxyphenyl group are known to be stabilizers of organic polymers normally subject to oxidative deterioration. U.S. Pat. No. 3,285,855 describes the manufacture and use of such compounds, particular of alkyl esters of hindered hydroxybenzoic and hydroxyphenylalkanoic acids, for the stabilization of synthetic organic polymers against oxidation, i.e. as antioxidants. These alkyl esters containing a hindered hydroxyphenyl group are employed in an amount of 0.01% to about 5% by weight, preferably about 0.01% to about 0.05% by weight based upon the stabilized mixture. The levels of stabilizer in the polymer may vary considerably depending on the particular end use application, the degree of protection desired, variations in substrate, and the presence of synergizing stabilizers such as thermal stabilizers or ultraviolet light absorbers, and dyes or pigments. The stabilized polymer compositions are prepared by a number of means, for example by mixing stabilizers into liquid substrates, by milling into thermoplastic substrates, or by dissolving in a co-solvent and mixing into a substrate solution.

The alkyl esters containing hindered hydroxyphenyl groups are usually handled in the form of a powder when admixed with polymer substrates. However, such powder form may pose certain difficulties during handling, packaging and transportation, as evidenced by possible dusting, caking and lump formation. It is therefore an object of the present invention to provide such hindered hydroxyphenyl group-containing alkyl esters in a convenient granulated form and to provide a process for the manufacture of such granules.

Several general methods are known for the manufacture of granules and related agglomerates. Granules may be formed from powders and other fine particles by suitable agitation in the presence of a binding liquid. Depending on the type of binding liquid, the liquid may remain in the agglomerates or be partially or totally removed by after-drying. Granules may be also formed from powders by pressurized compaction amd extrusion methods based on pressure. Application of heat to a powder may also result in sintering and formation of agglomerates of suitable size. Drying and solidification on surfaces may also lead to granular products. Solutions, suspensions or melts are applied to a heated or cooled surface, and the solids scraped off. In spray-drying, a pumpable and dispersible feed liquid, which may be a solution, gel, paste, emulsion, slurry or melt, is sprayed into a suitable chamber wherein solidification occurs. The chamber is heated in order to evaporate the solubilizing or emulsifying liquid, or else cooled to allow solidification of a melt. The latter process is also known as prilling and relies on a heat transfer between a cold gas, for example air, in the spray chamber, and the melt. Finally, granule formation is also feasible by agglomeration of liquid suspensions through changes in temperatures or by adding an immiscible liquid or a flocculant in order to change the surface tension properties of the liquid phase.

The conventional granulation methods have not, however, been satisfactory for the granulation of such low-melting alkyl esters containing a hindered hydroxyphenyl group.

The present invention has surprisingly overcome the difficulties by providing a process for the manufacture of granules of low-melting alkyl esters containing hindered hydroxyphenyl groups, which comprises introducing a melt of said ester into a cold agitated aqueous solution of an organic water-miscible solvent and then isolating the resulting granules.

Alkyl esters containing hindered hydroxyphenyl groups are, for example, compounds of the formula

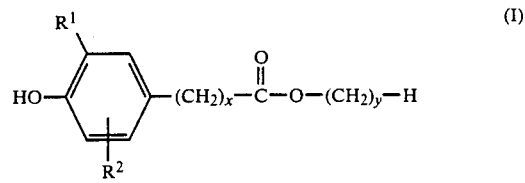

wherein $R^1$ and $R^2$, independent of each other, are lower alkyl of 1 to 8 carbon atoms, x is an integer from 0 to 6, and y is an integer from 6 to 30.

A lower alkyl group comprising 1 to 8 carbon atoms is, for example, methyl, ethyl, n-propyl, isopropyl, n-butyl, sec-butyl, tert-butyl or tert-pentyl. Preferred lower alkyl groups are those having 1 to 5 carbon atoms. Most preferred are alpha-branched lower alkyl groups, for example, isopropyl, tert-butyl or tert-pentyl.

The $R^2$ substituent may be located on the phenyl ring in the ortho or meta position relative to the hydroxy function. Preferably, $R^2$ is in the ortho position to the hydroxy group. The substituents $R^1$ and $R^2$ may represent the same or different lower alkyl groups as defined above. Preferably, both substituents $R^1$ and $R^2$ are methyl, isopropyl, tert-butyl or tert-pentyl, or one substituent is methyl and the other one is isopropyl, tert-butyl or tert-pentyl.

Compounds of the formula I are alkyl esters of hindered p-hydroxybenzoic acids if x is zero, or alkyl esters of hindered p-hydroxyphenylalkanoic acids if x is an integer from 1 to 6. Preferably, x is 1, 2 or 3, and in particular 2. The straight chain alkyl residue has from 6 to 30 carbon atoms. Preferably y is an integer from 6 to 20, in particular an even integer from 12 to 20, for example 16 or 18.

Particular mention is made of the compound of formula I wherein $R^1$ and $R^2$ are tert-butyl and are both in the ortho position to the hydroxy group, x is 2 and y is 18. This compound is octadecyl 3,5-di-tert-butyl-4-hydroxyhydrocinnamate, an antioxidant widely used in the plastics industry for the stabilization of synthetic organic polymers, and has a melting point of 50°–55° C.

A low-melting alkyl ester containing hindered hydroxyphenyl groups has, for example, a melting point anywhere between 20° C. and 100° C. Preferably the melting point is in the range of 30° C. to 80° C., for example around 50° C. It is understood that the process of the invention applies also to the alkyl esters having a melting point above 100° C. when in a pure state, but which contain manufacturing by-products or impurities which lower the melting point. Such impurities are, for example, homologous alkyl esters wherein y is different from the value of y of the primary compound.

In the process of the invention, the temperature of the melt is preferably 5° to 30° C. above the melting point of the compound to be granulated, usually around 10° C.

above the melting point so as to avoid unintentional crystallization and clogging in the melt.

The organic water-miscible solvent applicable to the invention is, for example, methanol, ethanol, isopropanol, acetone, acetonitrile or ethylene glycol. Preferred is a volatile organic solvent with a boiling point above the melting point of the compound to be granulated. For example, for compounds to be granulated having a melting point below 60° C., methanol is the preferred organic solvent, and for compounds having a melting point between 50° C. and 75° C., ethanol is the preferred organic solvent. The ratio of water to organic solvent is so chosen as to result in the desired granule particle size and size distribution and will depend on the organic solvent chosen and the compound to be granulated.

The temperature of the agitated aqueous solution is kept below room temperature, i.e. 20° C. The temperature is preferably kept between 5° C. and 15° C. The solution is agitated in a manner causing turbulence. Any kind of equipment used for agitation is suitable, for example conventional stirring at 50 rpm or more, and preferably about 300 rpm.

The granule formation is preferably conducted under conditions wherein the melt is introduced in amounts of less than 5%, by weight, of the solvent, particularly about 2% or less.

Proper granulation occurs rapidly, for example, in about 0.5 minutes. More time may be required for granule curing when the ratio of water to organic solvent is not at its optimum value or when the concentration of the melt introduced into the aqueous solvent is above 2%. Nevertheless, proper granulation is still accomplished within reasonable periods of time, for example within 3 to 5 minutes.

The solution containing the formed granules is then filtered, and the granules optionally sorted according to size. Oversized agglomerates may be returned to the melt. Undersized granules may also be returned to the melt, but are preferentially used as crystallization seeds suspended in the aqueous solution for further granulation.

The process of the invention may be conducted batchwise or in a continuous flow system. In a preferred embodiment of the invention, the melt of the compound to be granulated is added to the cold agitated aqueous solution in a continuous flow system so as to keep the ratio of melt and solvent in the desired range. After separation of the granules, the aqueous solvent optionally containing compound dust may be recirculated for further uptake of melt.

In a further preferred embodiment, the present invention relates to a process wherein the compound to be granulated is octadecyl 3,5-di-tert-butyl-4-hydroxyhydrocinnamate and wherein the cold aqueous solution is aqueous methanol kept at a temperature below 15° C. In this embodiment, the temperature of the melt of the compound to be granulated may be between 55° C. and 80° C., and is preferably between 60° and 65° C. It is usually produced by melting a wet cake of the compound containing 5-15% methanol, but can likewise be prepared by melting pure, dry compound or a wet cake containing more than 15% methanol, for example around 30% methanol.

In the preferred embodiment, the aqueous methanol contains between 5 and 20% water. As the water concentration decreases, the particle size decreases and the required time for granule formation increases. The particle size can therefore be determined by the amount of water in aqueous methanol. A preferred amount of water is around 10%, for example between 8 and 12%. The temperature of the aqueous methanol is kept at below 15° C. by external cooling. A convenient temperature is between 5° and 15° C. It has been found that the precise temperature of the solvent is not critical as long as it is kept below 15° C. and hence may be varied in a broad range without changing the size and properties of the granules formed. Granulation is achieved usually within 0.5 minutes. Additional time is required for granule curing when the amount of melt introduced into the aqueous methanol is greater than 2%.

In a convenient continuous flow system, octadecyl 3,5-di-tert-butyl-4-hydroxyhydrocinnamate is melted and added to a primary granulation vessel containing agitated aqueous methanol. The mixture is continuously transferred to a secondary granulation vessel for curing, then pumped through a product screener in order to separate and collect oversize granules and aggregates and granules of the desired size. Aqueous methanol containing dust is collected in a surge tank, then cooled to the desired temperature and recirculated to the primary granulation vessel after adjusting the methanol and water content. The flow of the melt and of aqueous methanol is adjusted so as to provide the desired ratio of melt and solvent and the desired curing time for the formed granules.

In a further aspect, the invention relates to free-flowing, dust-free granules of a low-melting alkyl ester containing hindered hydroxyphenyl groups. Preferred are free-flowing, dust-free granules of those compounds which are mentioned above as being preferred in the process of the invention, in particular granules of octadecyl 3,5-di-tert-butyl-4-hydroxyhydrocinnamate. The free-flowing, dust-free granules may be obtained by the process described above. The granules of the invention are preferably of a size between 10 and 60 mesh (U.S. Standard Sieve Series).

The following examples are intended to illustrate the invention and are not to be construed as being a limitation thereof. Percentages and parts are given by weight.

EXAMPLE 1

REACTION CONDITIONS FOR THE GRANULATION OF OCTADECYL 3,5-DI-TERT-BUTYL-4-HYDROXYHYDROCINNAMATE

The title compound is prepared according to U.S. Pat. No. 3,285,855 and is used as a wet cake containing 10% methanol. The compound is an off-white powder melting at 50°-55° C. The wet cake is melted at 60°-65° C. and added in a slow stream in a given concentration of between 0.59% and 2.65% to a continuous stream of aqueous methanol containing between 5% and 20% water kept at a temperature between 8° C. and 20° C. in two consecutive 2 liter round bottom jacketed reactors stirred at 300 rpm resulting in a turbulent state. The retention time in the reactors is calculated by the formula $$\frac{4000 \text{ ml}}{(\text{melt ml/min} + \text{solvent ml/min})}$$

and is between 0.52 and 2.25 min. Approximately 6 liter of solvent and 1 liter of melt are used for each test. The solids are sieved through a 50 mesh U.S. Standard Sieve and dried in a fluidized bed dryer. The undersized material is continuously recycled in the aqueous methanol. The dried solids are sieved through 10 mesh and 60 mesh sieves (U.S. Standard Sieve Series) and the relative amounts determined. The results are collected in the table:

TABLE

| | | | | | Size Distribution of Granules | | |
|---|---|---|---|---|---|---|---|
| Experiment Number | Solvent Composition (% water) | Solvent Temperature (°C.) | Retention time (min) | Conc. of melt (%) | >10 mesh (%) | Granule Size 10–60 mesh (%) | <60 mesh (%) |
| 1 | 20 | 8 | 0.55 | 2.65 | 59.3 | 40.1 | 0.6 |
| 2 | 5 | 20 | 0.52* | 2.65 | 35 | 50.8 | 14.2 |
| 3 | 5 | 8 | 0.52* | 2.65 | 0.4 | 68.1 | 31.5 |
| 4 | 5 | 8 | 0.53 | 0.74 | 0.4 | 98.3 | 1.3 |
| 5 | 20 | 20 | 0.56 | 0.74 | 56.5 | 43.3 | 0.2 |
| 6 | 20 | 20 | 0.55 | 2.65 | 52.2 | 47.5 | 0.3 |
| 7 | 5 | 20 | 0.53* | 0.74 | 2.8 | 73.9 | 23.3 |
| 8 | 10 | 10 | 0.54* | 1.48 | 16.9 | 81.6 | 1.5 |
| 9 | 10 | 10 | 0.93* | 2.58 | | no granules isolated | |
| 10 | 10 | 10 | 0.95 | 0.88 | 1.9 | 97 | 1.1 |
| 11 | 10 | 10 | 2.21 | 1.48 | 4.8 | 94.7 | 0.5 |
| 12 | 5 | 10 | 2.25 | 1.48 | 14.8 | 84.8 | 0.4 |
| 13 | 10 | 10 | 0.95 | 0.59 | 0.2 | 99.2 | 0.6 |
| 14 | 10 | 10 | 1.43 | 2.23 | 6.1 | 93.4 | 0.5 |

*Retention time insufficient for complete granule curing.

EXAMPLE 2

CONTINUOUS FLOW GRANULATION OF OCTADECYL 3,5-DI-TERT-BUTYL-4-HYDROXYHYDROCINNAMATE

The title compound in the form of a wet cake containing 10% methanol is charged into a 6000 gal. product reactor under a nitrogen atmosphere. The reactor is slowly heated to 60° C. with steam, and the melt agitated at slow speed. A 1000 gal. surge tank is charged with methanol and the water concentration adjusted to 10% corresponding to a specific gravity of 0.820 at 20° C. The solvent is cooled to 5° C. using a recirculation cooler charged with brine, then circulated at a flow rate of 160 gal. per min. through a first granulation vessel holding 300 gal., a second granulation vessel holding 300 gal., both equipped with an agitator set to 350 rpm, and a product screener separating 10 mesh oversize granules and desired −10−+60 mesh granules, all swept with nitrogen. The melt is then added to the solvent in the first granulation vessel at a flow rate of 2.5 gal. per min. The recirculated solvent in the surge tank contains −60 mesh undersize product and is checked for water content and adjusted accordingly in regular intervals. The system has a turn-over of 1200 lb. per hour and gives 93–95% free-flowing granules of −10+60 mesh size and 5–7% oversize agglomerates, which are collected and added to the melt.

What is claimed is:

1. A process for the manufacture of granules of low-melting alkyl ester containing hindered hydroxyphenyl groups, which comprises introducing a melt of said ester into aqueous methanol containing between 8 and 12% water maintained under a turbulent state at a temperature below 15° C. and then isolating the resulting granules.

2. The process according to claim 1 wherein the alkyl ester containing hindered hydroxyphenyl groups is a compound of the formula

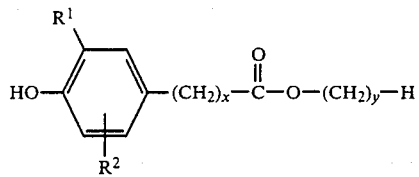

(I)

wherein $R^1$ and $R^2$, independent of each other, are lower alkyl of 1 to 8 carbon atoms, x is an integer from 0 to 6, and y is an integer from 6 to 30.

3. The process according to claim 2 wherein $R^2$ is in an ortho position to the hydroxy function, x is 1, 2 or 3, and y is an integer from 6 to 20.

4. The process according to claim 1 wherein the melting point of the alkyl ester containing hindered hydroxyphenyl group is between 20° C. and 100° C.

5. The process according to claim 4 wherein the melting point is between 30° C. and 80° C.

6. The process according to claim 1 wherein the temperature of the aqueous methanol is between 5° C. and 15° C.

7. The process according to claim 1 wherein the alkyl ester is octadecyl 3,5-di-tert-butyl-4-hydroxy-hydrocinnamate.

8. The process according to claim 7 wherein the temperature of the melt is between 55° C. and 80° C.

9. The process according to claim 8 wherein the temperature of the melt is between 60° C. and 65° C.

10. The process according to claim 1 wherein the aqueous methanol contains around 10% water.

11. The process according to claim 7 wherein the melt introduced into aqueous methanol does not exceed 5%.

12. The process according to claim 11 wherein the melt introduced into aqueous methanol does not exceed 2%.

13. The process according to claim 1 wherein the melt is introduced into aqueous methanol in a continuousflow system.

* * * * *